(12) United States Patent
Kotidis

(10) Patent No.: US 10,402,543 B2
(45) Date of Patent: Sep. 3, 2019

(54) METHOD AND SYSTEM FOR PAY-PER-USE PRESCRIPTION VALIDATION

(71) Applicant: Volcano Corporation, San Diego, CA (US)

(72) Inventor: Petros Kotidis, Framingham, MA (US)

(73) Assignee: VOLCANO CORPORATION, San Diego, CA (US)

( * ) Notice: Subject to any disclaimer, the term of this patent is extended or adjusted under 35 U.S.C. 154(b) by 961 days.

(21) Appl. No.: 14/588,127

(22) Filed: Dec. 31, 2014

(65) Prior Publication Data

US 2015/0112714 A1    Apr. 23, 2015

Related U.S. Application Data

(63) Continuation of application No. 11/626,660, filed on Jan. 24, 2007.

(51) Int. Cl.
*G06F 19/00*    (2018.01)
*G06Q 50/22*    (2018.01)
*G06Q 30/04*    (2012.01)

(52) U.S. Cl.
CPC ......... *G06F 19/3456* (2013.01); *G06Q 30/04* (2013.01); *G06Q 50/22* (2013.01)

(58) Field of Classification Search
CPC ............. G06F 19/3456; G06F 19/3475; G06F 19/322–327; G06Q 50/22–24; G06Q 30/04; G16H 20/10
See application file for complete search history.

(56) References Cited

U.S. PATENT DOCUMENTS

| | | | |
|---|---|---|---|
| 4,796,181 A * | 1/1989 | Wiedemer | G06F 21/10 380/230 |
| 5,925,127 A | 7/1999 | Ahmad | |
| 6,771,369 B2 * | 8/2004 | Rzasa | G01J 3/02 250/339.07 |
| 7,028,723 B1 | 4/2006 | Alouani et al. | |
| 2002/0091699 A1 | 7/2002 | Norton et al. | |
| 2002/0137497 A1 | 9/2002 | Gillespie | |
| 2003/0055683 A1 | 3/2003 | Gibson et al. | |
| 2008/0162473 A1 | 7/2008 | Fitzer et al. | |
| 2009/0080735 A1 * | 3/2009 | Chapman | G06T 7/0004 382/128 |

* cited by examiner

*Primary Examiner* — Sheetal R Paulson

(57) ABSTRACT

A business model for facilitating the deployment of prescription validation systems into pharmacies is installed in pharmacies for little or no up-front cost to the pharmacy. Instead, the pharmacy is charged on a per use basis, that is, charged every time a prescription is validated in the system. In this way, the system vendor obtains payment on a subscription-like basis. Up-front costs at the pharmacy are avoided. Moreover, risks to a pharmacy concerning maintenance and slow productivity are avoided, or shifted onto the system owner, who is able to assess those risks.

8 Claims, 2 Drawing Sheets

METHOD AND SYSTEM FOR PAY-PER-USE PRESCRIPTION VALIDATION

CROSS-REFERENCE TO RELATED APPLICATION

This application is a continuation of U.S. patent application Ser. No. 11/626,660, filed Jan. 24, 2007, the entirety of which is hereby incorporated by reference herein.

BACKGROUND OF THE INVENTION

Improperly filled prescriptions represent a substantial risk of injury to customers at pharmacies. Filling prescriptions is a generally commoditized business where the objective is to maximize the number of prescriptions filled by each pharmacist per hour. It is inevitable that some prescriptions are filled with the incorrect drugs or medication.

To address this problem, systems for the validation of prescriptions have been proposed. For example, U.S. Pat. No. 6,771,369 concerns a system and method for pharmacy validation and inspection. The disclosed system provides a combination of a bar code reader and a spectroscopy system. In operation, a container of pills is provided with a label containing prescription information for a specific patient. The label is read by the system's bar code reader. Contemporaneously, the spectral response of the pills contained within the container is also resolved. A data analysis system then compares the information from the bar code reader with the spectral response information to ensure that the chemical content of the pills within the container matches the prescription. Such systems provide a way of confirming the accuracy of a filled prescription. Specifically, they insure that the contents of the container match the container's label. In this way, errors in prescriptions could be reduced.

SUMMARY OF THE INVENTION

The main impediment to the market penetration of prescription validation systems into the typical pharmacy is the cost of such systems. While there might be savings in terms of the pharmacy's liability insurance because of the decrease in the pharmacy's errors, the systems are comparatively expensive and represent an up-front cost to the typical pharmacy. Further, it is often unclear whether such systems will work accurately enough and at the speeds required in the pharmacy to justify investment. There are also risks to the pharmacy concerning costs of ownership including maintenance and equipment downtime.

The present invention is directed to a business model for facilitating the deployment of prescription validation systems into pharmacies. Specifically, these systems are installed in pharmacies for little or no up-front cost to the pharmacy. Instead, the pharmacy is charged on a per use basis, i.e., charged every time a prescription is validated in the system or based on entirely or in part on the number of validations performed. In this way, the system vendor obtains payment on a subscription basis. At the same time, up-front costs at the pharmacy are avoided. Moreover, risks to a pharmacy concerning maintenance and slow productivity are avoided, or shifted onto the system owner, who is able to assess those risks.

Payment per validation business model is similar to other business models used in the pharmacy industry. For example, currently, a process of "adjudication" is used whereby a pharmacist confirms the level of insurance of a given customer. Specifically, when a customer seeks to fill a prescription, the pharmacist will usually contact an insurance information clearing house, which provides the pharmacist with information concerning the level of coverage for that specific customer. In this way, the pharmacy can handle prescriptions from customers having different insurance and different coverage levels, while being assured that the insurance company will provide the expected level of reimbursement.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
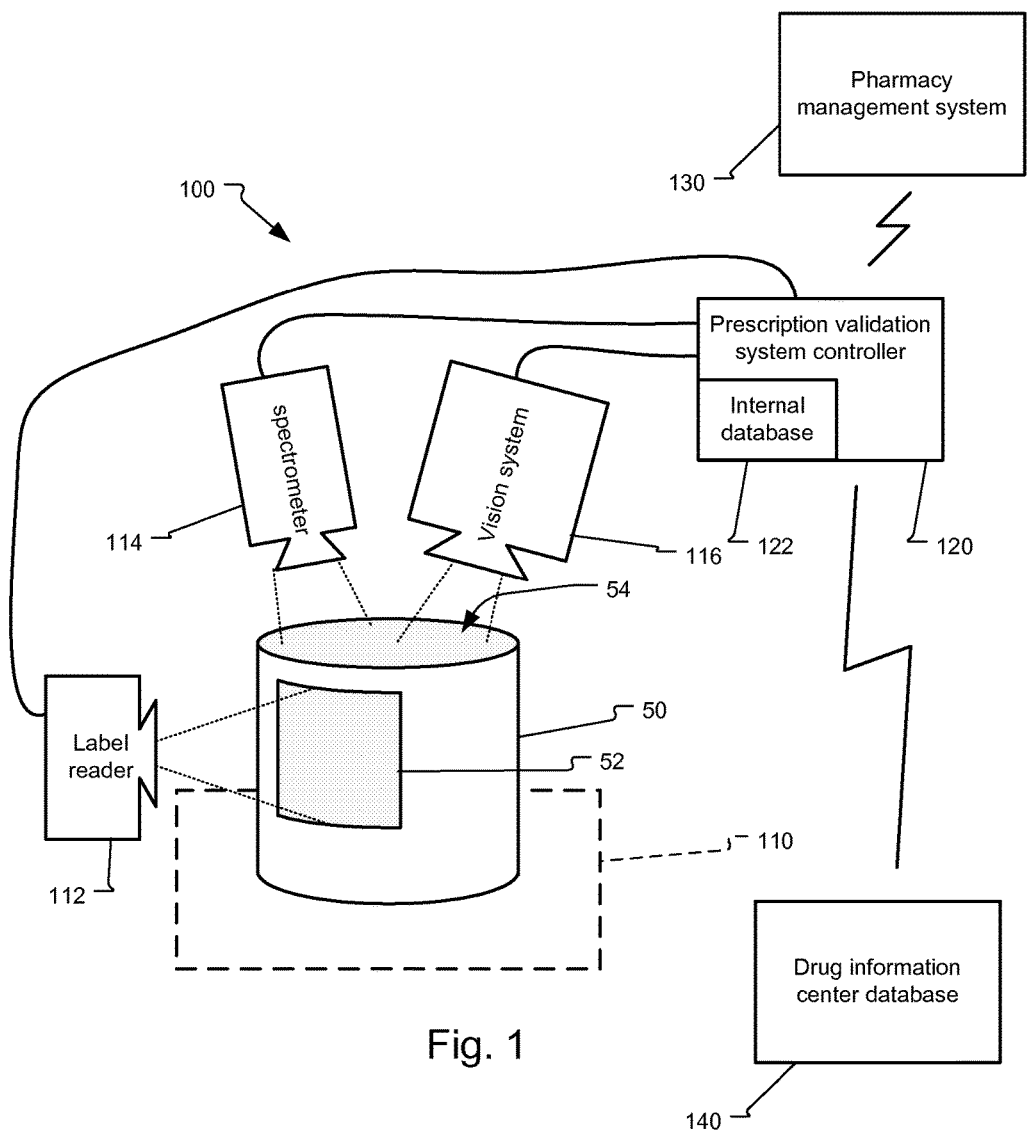
FIG. 1 is a schematic diagram of a prescription validation system used in the present invention.

FIG. 1 shows a prescription validation system that is used in connection with the present invention, in one example.

The validation system 100 is used to analyze the contents of a container, such as a pill container 50. Specifically, in operation, a container 50, typically representing a filled prescription, with a prescription specific label 52 on its outer surface, is placed within an analysis area 110 of the validation system 100.

In one embodiment, both a spectrometer 114 and vision system 116 are oriented to view the contents of the container 50, usually near its mouth 54. The vision system 116 is used to check the shape, color, and symbols found on pills, for example, within the container 50. The spectrometer 114 is used to collect the spectroscopic response of those same drugs, such as pills, within the container 50.

Simultaneously or contemporaneously, in one embodiment, a label reader 112 reads the prescription information found on the label 52. In one example, the label reader has an optical character recognition (OCR) system to decode the human-readable information encoded on the label 52. In another example, the label reader alternatively, or in addition, comprises a machine code reading component such as a bar code reader that reads a machine-readable, e.g., bar code, found on the label 52.

The prescription information from the label reader 112, the spectroscopic information from the spectrometer 114, and the pill shape, color, and symbol information from the vision system 116 are analyzed by the prescription validation system controller 120. The controller 120 confirms whether the prescription has been properly filled. Specifically, the prescription information found on the label 52 is compared to the pill shape, color, and/or symbols that were determined by the vision system 116 and the composition of those pills as determined by the spectrometer 114.

According to the invention, the prescription validation system controller 120 connects to a pharmacy management system 130. This contains the pharmacy's database for the drugs and/or drugs held by the pharmacy and/or the existing customers serviced by the pharmacy. The prescription validation system controller 120 confirms the prescription information on the label 52 is consistent with this back office system, for example, based on scheduled prescriptions to be filled at the pharmacy. That is, in one embodiment, the pharmacy management system comprises customer information and pending prescriptions to be filled. These prescription orders are then assigned to pharmacists at each validation system 100. As prescriptions are validated, the pharmacy management system 130 updates the queue of prescriptions to be filled and confirms the validated prescriptions were to be filled.

The prescription validation system controller 120 is also connected to a drug information center database 140. In one example, connection is a data connection across a public network, such as the internet. In other examples, the connection is supported by a dial-up connection or other direct point-to-point data communication. This drug information center includes databases of spectroscopic pill information and pill shape, color and symbol information.

Figure 2:
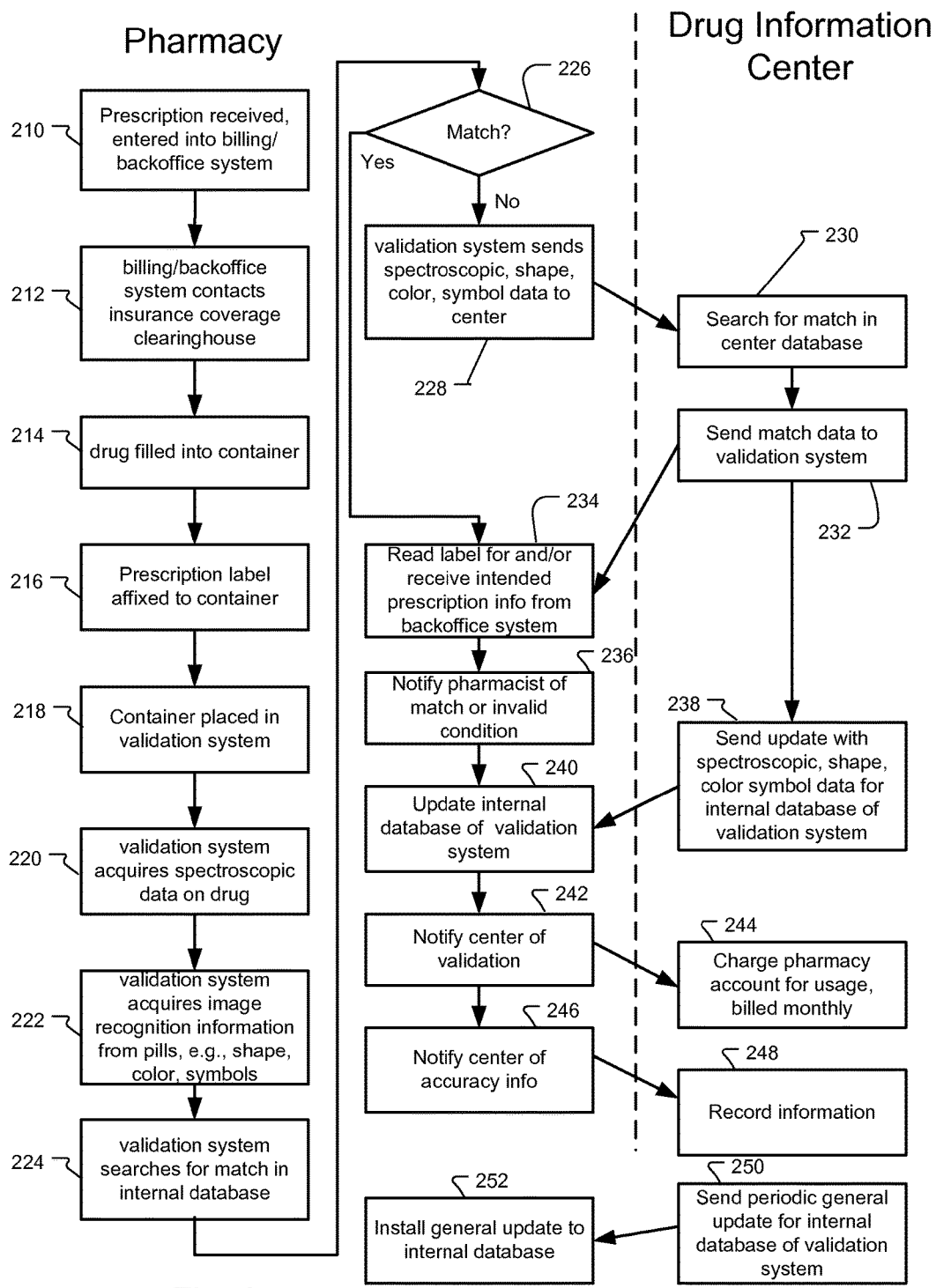
FIG. 2 is a flow diagram illustrating a method for prescription validation and charges to a pharmacy.

FIG. 2 shows the method of operation for the present invention.

As is common, in step 210, a prescription is received and entered into the billing/back office pharmacy management system 130 of the pharmacy. Most pharmacies have such a database system that stores previous prescriptions by a patient, the number of refills left on those prescriptions, insurance information for patients, billing information, and other account information. The system also controls pharmacy workflow in some examples so that prescriptions to be filled are distributed among the working pharmacists.

Then, the billing/back office pharmacy management system 130 contacts an insurance coverage clearing house. This step is often referred to as adjudication where the pharmacy determines whether the patient is covered, the insurance company, and the level of coverage to determine the level of reimbursement that the pharmacy will be receive from the customers' insurance.

Then in step 214, the drug is dispensed. Often, this filling is performed manually by pharmacist who puts a prescribed number of pills, for example, into the container 50. In step 216, pharmacist affixes the label 52 to the container 50. Often this label 52 is printed directly by the billing/back office system 130 for the pharmacy.

In other examples, the steps of filling the container and/or printing and affixing the prescription label 52 to the container 50 are performed by an automated system. Especially in large pharmacies, there are machines that take entered prescription information and then automatically dispense the drugs into the containers 50, including the required labels 52. In step 218, the container 50 is placed in the analysis area 110 (see FIG. 1).

In step 220, the validation system 100 acquires a spectroscopic data of the drug. Specifically the spectrometer 114 determines the spectral response of the pills contained in the container 50.

In step 222, the validation system 100 also preferably acquires image information for the pills using the vision system 116. Preferably this image recognition information includes the shape, color and any symbols contained on the pills.

Based on the spectroscopic and image information, the validation system controller 120 searches for a match in an internal database 122 in step 224. The system then determines whether or not there is a match for the pills based on the color, shape, symbols on the pills and/or the spectroscopic data on the pills in step 226. If no match is found, then in step 228, the validation system sends the spectroscopic, shape, color data, to the drug information center 140.

In step 230 the drug information center 140 receives this spectroscopic and/or image recognition information from the validation system in step 230. It searches in the center's database for a match. The drug center 140 then sends match information to the validation system 100 in step 232 or signals an error condition with no match being found.

In the event of a non-match at the center's database, the center 140 signals for a recalibration of the validation system 100, usually including a recalibration of the spectroscopy system 114.

Based upon the match information from the drug center 140 or determined internally by reference to the database 122 of the validation system controller 120, in step 224, the validation system 100 reads the label 52 and/or receives intended prescription information from the billing/back office system 130. Specifically, the validation system 100 or management system 130 validates that a request for this prescription exists, that the drugs in the container match both the label 52 on the container 50 and the intended prescription in the back office system 130.

Then in step 236, the validation system 100 notifies the pharmacist of a match or an invalid condition. That is, if there is a detected error in the data, the system signals that the particular prescription has not been properly filled.

In step 238, the drug center 140 also sends an update with the spectroscopic, shape, and color symbol data for the internal database 122 of the validation system controller 120. Specifically, the drug center 140 updates the internal database 122, in one embodiment, of the validation system controller 120 based upon the requests that the validation sent in 228. In this way, the validation system controller will signal a match if a similar drug is presented to the validation system in the future. In step 240, the validation system controller 120 then updates its internal database 122 with the new spectroscopic, shape, color and symbol data from the drug center 140.

According to the step 242, the validation system controller 120 notifies the drug information center 140 of the validation. In step 224, the drug information center updates the pharmacy's billing information with this validation. In one embodiment, the center 140 periodically sends a bill to the pharmacy. The charges are based on the number of validations that were performed over the billing period. In other examples the bill also includes rental or lease changes for the validation system 100 for the billing period.

Often, the validations will cost only a few cents. Also, in one embodiment, the pharmacy system notifies the center with accuracy information concerning the accuracy with which prescriptions are being filled at the pharmacy and any errors originating from the validation system 100 in step 246.

In step 248, the drug center further updates its record information with this information from the local validation system at their pharmacy.

In step 250, the drug information center 140 periodically sends general updates for the internal database of the validation system. These internal updates are used, in one embodiment, to increase the probability of a match when the validation system 100 interrogates its internal database. For example, as the composition of pills, specifically pill coatings change, and/or with changes in color and introduction of instruction of new and generic pills, this information is continually sent by the drug information center 140 to update the internal database 122 of each validation system 100 at each pharmacy. Then, finally, in step 252, the pharmacy validation system updates its internal database with the new data for its validation system.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for prescription validation, the method comprising:
    receiving, at a drug information center, a notification representative of a prescription validation from a validation system, the notification representative of the prescription validation being generated by the validation system in response to the validation system:
        reading a label of a container using a label reader;
        determining the spectroscopic response of the contents of the container using a spectroscopy system;
        determining at least one of the shape, color, or symbols of the contents of the container using a vision system;
        identifying, in an internal database of the validation system, a match between the spectroscopic response and the at least one of the shape, color, or symbols, wherein identifying the match includes determining that the spectroscopic response and the at least one of the shape, color, or symbols are representative of the same contents;
        determining if the label corresponds to the contents of the container by comparing the label and the match; and
        determining that a request for a prescription corresponding to the contents of the container exists and that the request corresponds to the label and the match;
    receiving, at the drug information center, when the validation system cannot identify a match in the internal database, the spectroscopic response and the at least one of the shape, color, or symbols;
    identifying, in an external database of the drug information center different from the internal database, an alternative match between the spectroscopic response and the at least one of the shape, color, or symbols, wherein identifying the match includes determining that the spectroscopic response and the at least one of the shape, color, or symbols are representative of the same contents;
    transmitting the alternative match to the validation system such that the validation system can determine if the label corresponds to the contents of the container by the comparing the label and the match, and such that the validation system can determine that the request for the prescription corresponding to the contents of the container exists and that the request corresponds to the label and the alternative match;
    transmitting update data representative of the alternative match to the validation system such that the internal database of the validation system is updated with the update data to identify the alternative match in the future based on the spectroscopic response and the at least one of the shape, color, or symbols;
    transmitting billing information for use of the validation system, the billing information including a predetermined dollar cost per prescription validation and any cost of installation, maintenance, and continued use of the validation system;
    collecting, at the drug information center, the notifications representative of the prescription validations received from the validation system over a billing period;
    transmitting a bill corresponding to the billing period based in part on a number of prescription validations performed over the billing period and in part on any cost for installation, maintenance, and continued use of the validation system.

2. The method of claim 1, further comprising:
    periodically transmitting general update data to the validation system, the general update data including information representative of at least one of a composition of a drug, a coating of a drug, a color of a drug, a new drug, a generic drug, such that the internal database of the validation system is updated with the general update data to identify contents of the container using the general update data.

3. The method of claim 1, further comprising:
    transmitting a recalibration signal to the validation system when the drug information center cannot identify the alternative match in the external database of the drug information center.

4. The method of claim 1, wherein reading a label of a container using a label reader includes at least one of:
    decoding human-readable information encoded on the label using an optical character recognition (OCR) system; and
    decoding machine-readable information encoded on the label using a machine code reading component.

5. A method for prescription validation, the method comprising:
    validating a prescription at a validation system, including:
        reading a label of a container using a label reader;
        determining the spectroscopic response of the contents of the container using a spectroscopy system;
        determining at least one of the shape, color, and the symbols of the contents of the container using a vision system;
        identifying, in an internal database of the validation system, a match between the spectroscopic response and the at least one of the shape, color, or symbols, wherein identifying the match includes determining that the spectroscopic response and the at least one of the shape, color, or symbols are representative of the same contents;
    transmitting, to a drug information center, when the match cannot be identified in the internal database, the spectroscopic response and the at least one of the shape, color, or symbols;
    receiving, at the validation system, an alternative match between the spectroscopic response and the at least one of the shape, color, or symbols, the alternative match identified in an external database of the drug information center different from the internal database, wherein the alternative match is identified by determining that the spectroscopic response and the at least one of the shape, color, or symbols are representative of the same contents;
    receiving, at the validation system, update data representative of the alternative match such that the internal database of the validation system is updated with the update data to identify the alternative match in the future based on the spectroscopic response and the at least one of the shape, color, or symbols;

determining if the label corresponds to the contents of the container by comparing the label and at least one of the match and the alternative match; and determining that a request for a prescription corresponding to the contents of the container exists and that the request corresponds to the label and at least one of the match and the alternative match;

transmitting, to the drug information center, a notification representative of a prescription validation;

repeating the transmitting the notification step for prescriptions validations over a billing period;

receiving, from the drug information center, billing information for use of the validation system, the billing information including a predetermined dollar cost per prescription validation and any cost of installation, maintenance, and continued use of the validation system;

receiving, from the drug information center, a bill corresponding to the billing period based in part on a number of prescription validations performed over the billing period and the in part on any cost for installation, maintenance, and continued use of the validation system.

6. The method of claim 5, further comprising:

periodically receiving general update data from the drug information center, the general update data including information representative of at least one of a composition of a drug, a coating of a drug, a color of a drug, a new drug, a generic drug, such that the internal database of the validation system is updated with the general update data to identify contents of the container using the general update data.

7. The method of claim 5, further comprising:

receiving a recalibration signal when the drug information center cannot identify the alternative match in the external database of the drug information center.

8. The method of claim 5, wherein reading a label of a container using a label reader includes at least one of:

decoding human-readable information encoded on the label using an optical character recognition (OCR) system; and decoding machine-readable information encoded on the label using a machine code reading component.

* * * * *